(12) United States Patent
Ohl et al.

(10) Patent No.: US 10,076,468 B2
(45) Date of Patent: Sep. 18, 2018

(54) MEDICATION DISPENSER BRACELET WITH VIBRATING ALARM AND BLUETOOTH COMMUNICATION

(71) Applicants: Malena Danielle Ohl, Boston, MA (US); Wesley Victor Wilson, Markham (CA); Margaret Davis Schoening, Cambridge, MA (US); Andreas Loeve Selvik, Cambridge (GB); Seunghyuk Noh, Providence, RI (US)

(72) Inventors: Malena Danielle Ohl, Boston, MA (US); Wesley Victor Wilson, Markham (CA); Margaret Davis Schoening, Cambridge, MA (US); Andreas Loeve Selvik, Cambridge (GB); Seunghyuk Noh, Providence, RI (US)

(*) Notice: Subject to any disclaimer, the term of this patent is extended or adjusted under 35 U.S.C. 154(b) by 0 days.

(21) Appl. No.: 15/404,515

(22) Filed: Jan. 12, 2017

(65) Prior Publication Data
US 2017/0196774 A1     Jul. 13, 2017

Related U.S. Application Data

(60) Provisional application No. 62/388,000, filed on Jan. 13, 2016.

(51) Int. Cl.
*G07F 11/00* (2006.01)
*G04B 47/00* (2006.01)
(Continued)

(52) U.S. Cl.
CPC ............ *A61J 7/0481* (2013.01); *A44C 5/003* (2013.01); *A44C 5/0023* (2013.01);
(Continued)

(58) Field of Classification Search
CPC ...... A61J 7/0481; A61J 7/0418; A61J 7/0436; A61J 7/0076; A61J 7/0069; A61J 2200/30; A44C 5/0023; A44C 5/003; G08B 6/00
(Continued)

(56) References Cited

U.S. PATENT DOCUMENTS 3,009,614 A * 11/1961 Humphner ............. A44C 5/003
                                                        224/219
3,402,808 A * 9/1968 Yannuzzi ............... A61B 5/117
                                                        206/232

(Continued)

OTHER PUBLICATIONS

Victoria Gomelsky, "Going from Smart to Smarter: Jewelry Enters the Wearable Technology Market." The New York Times, Dec. 4, 2014.

*Primary Examiner* — Rakesh Kumar
(74) *Attorney, Agent, or Firm* — Yale Yechiel N. Robinson

(57) ABSTRACT

The present invention is a bracelet that contains a cartridge holding a plurality of interior storage compartments that are each designed to hold one or more pills. A sliding door is used to withdraw the pills from any one compartment at a time. The bracelet comprises electronic components that enable it to activate a vibrating alarm at a prearranged time to remind the user to take her pills, and to track when the door has been opened to withdraw the pills, and to communicate the alarm and tracking information to an external electronic device, such as a mobile phone, via Bluetooth wireless communication.

3 Claims, 5 Drawing Sheets

(51) Int. Cl.
*A61J 7/04* (2006.01)
*A61J 7/00* (2006.01)
*A44C 5/00* (2006.01)
*G08B 6/00* (2006.01)

(52) U.S. Cl.
CPC ........... *A61J 7/0069* (2013.01); *A61J 7/0076* (2013.01); *A61J 7/0418* (2015.05); *A61J 7/0436* (2015.05); *G08B 6/00* (2013.01); *A61J 2200/30* (2013.01)

(58) Field of Classification Search
USPC .......................................................... 221/2
See application file for complete search history.

(56) References Cited

U.S. PATENT DOCUMENTS

| | | | |
|---|---|---|---|
| 3,680,751 A * | 8/1972 | Ten Brook | A44C 5/003 206/540 |
| 4,427,130 A | 1/1984 | Szigeti | |
| 4,682,299 A | 7/1987 | McIntosh | |
| 5,646,912 A * | 7/1997 | Cousin | A61J 7/0481 221/15 |
| 5,802,014 A * | 9/1998 | Danko | A44C 5/003 224/165 |
| 6,234,343 B1 | 5/2001 | Papp | |
| 6,340,242 B1 * | 1/2002 | Sandidge | G04B 37/127 368/223 |
| 6,421,650 B1 | 7/2002 | Goetz | |
| 6,601,729 B1 | 8/2003 | Papp | |
| 6,859,136 B2 | 2/2005 | Gastel | |
| 6,945,426 B2 * | 9/2005 | Gentzkow | A61J 7/0046 220/751 |
| 7,196,972 B2 * | 3/2007 | Pitocco | G04G 11/00 368/10 |
| 7,269,476 B2 | 9/2007 | Ratnakar | |
| 7,302,311 B2 | 11/2007 | Varis | |
| 7,542,379 B2 * | 6/2009 | Kimel | A61J 7/0481 224/165 |
| 7,978,564 B2 | 7/2011 | De La Huerga | |
| 8,055,380 B1 | 11/2011 | Verma | |
| 8,326,574 B2 | 12/2012 | Hogebrink | |
| 8,556,120 B2 | 10/2013 | Ando | |
| 8,708,192 B2 | 4/2014 | Flowers | |
| D710,235 S * | 8/2014 | Rummonds | D11/2 |
| 8,823,510 B2 | 9/2014 | Downey | |
| 9,393,180 B2 | 7/2016 | Lapham | |
| 9,460,581 B2 | 10/2016 | Niinisto | |
| 9,549,051 B2 | 1/2017 | Mercando | |
| 9,554,969 B2 | 1/2017 | Lehmann | |
| 9,582,035 B2 | 2/2017 | Connor | |
| 2002/0088737 A1 * | 7/2002 | Stepp | A61J 1/035 206/538 |
| 2011/0032104 A1 | 2/2011 | Cho | |
| 2013/0075437 A1 | 3/2013 | Zinnerman | |
| 2013/0086943 A1 | 4/2013 | Turney | |
| 2013/0154826 A1 | 6/2013 | Ratajczyk | |
| 2014/0101755 A1 | 4/2014 | Tang | |
| 2015/0341903 A1 | 5/2015 | Jeong | |
| 2015/0289227 A1 | 10/2015 | Becker | |
| 2015/0296480 A1 | 10/2015 | Kinsey | |
| 2017/0196774 A1 * | 7/2017 | Ohl | A61J 7/0481 |

* cited by examiner

MEDICATION DISPENSER BRACELET WITH VIBRATING ALARM AND BLUETOOTH COMMUNICATION

BACKGROUND INFORMATION

Field of the Invention

The present invention relates to medication dispensers, and more particularly, relates to a medication dispenser in the form of a wearable electronic bracelet.

Description of the Prior Art

Electronic medication dispensers, typically pill boxes, may comprise alarms (for example: vibrators, beepers, and/or visual displays) to remind the user to take her pill at the prescribed time and correct dose. Many electronic medication dispensers have the additional feature of tracking the user's compliance by signaling to a computer (or any electronic storage medium) when the user has opened the pill box to take her medication. The computer that activates the alarm and tracks the user's compliance may be physically attached to the pill box, as in U.S. Pat. No. 9,393,180 invented by Lapham. Alternatively, the computer can activate the alarm and receive compliance tracking information via short-range wireless communication, as in U.S. Pat. No. 7,978,564 invented by De La Huerga. The latter patent discloses Bluetooth as one possible form of wireless communication.

Medication dispensers are known in various shapes and configurations. A medication dispenser in the annular shape of a ring or bracelet was disclosed in U.S. Pat. No. 4,427,130 invented by Szigeti. More recent designs of bracelets comprising a container to hold small objects are disclosed in U.S. Application 20130075437 invented by Zinnerman, and U.S. Application 20130086943 invented by Turney. Each of the three bracelet designs referenced in this paragraph comprise only one storage compartment, and are thus distinguishable from the present invention which discloses a cartridge holding a plurality of small storage compartments, each of which is intended to hold one pill or one dose of pills.

The idea of reminding a user to take her medication by causing a bracelet to vibrate is described in U.S. Application 20140158703 by Niinisto ("The patient can be reminded to acknowledge the notification and/or to take the medications . . . by a separate reminder device, which can be, for example, a bracelet that contains a vibrator to remind the patient.") However, in that disclosure, the bracelet does not contain the medication.

BRIEF SUMMARY OF THE INVENTION

The present invention is a bracelet that contains a cartridge holding a plurality of interior storage compartments that are each designed to hold one or more pills. A sliding door is used to withdraw the pills from any one compartment at a time. The bracelet comprises electronic components that enable it to activate a vibrating alarm at a prearranged time to remind the user to take her pills, and to track when the door has been opened to withdraw the pills, and to communicate the alarm and tracking information to an external electronic device, such as a mobile phone, via Bluetooth wireless communication.

BRIEF DESCRIPTION OF THE DRAWINGS

These and other features and advantages of the present invention will be better understood by reading the following detailed description, taken together with the drawings wherein.

Figure 1:
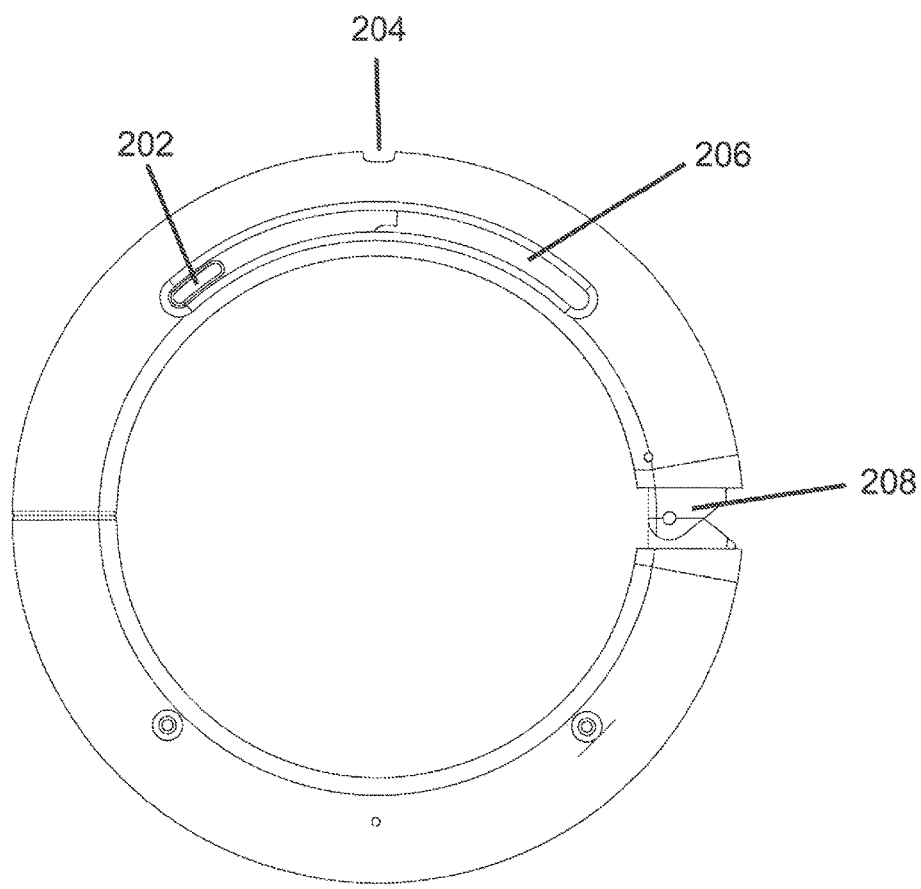
FIG. 1 is a side view of the bracelet.
Figure 2:
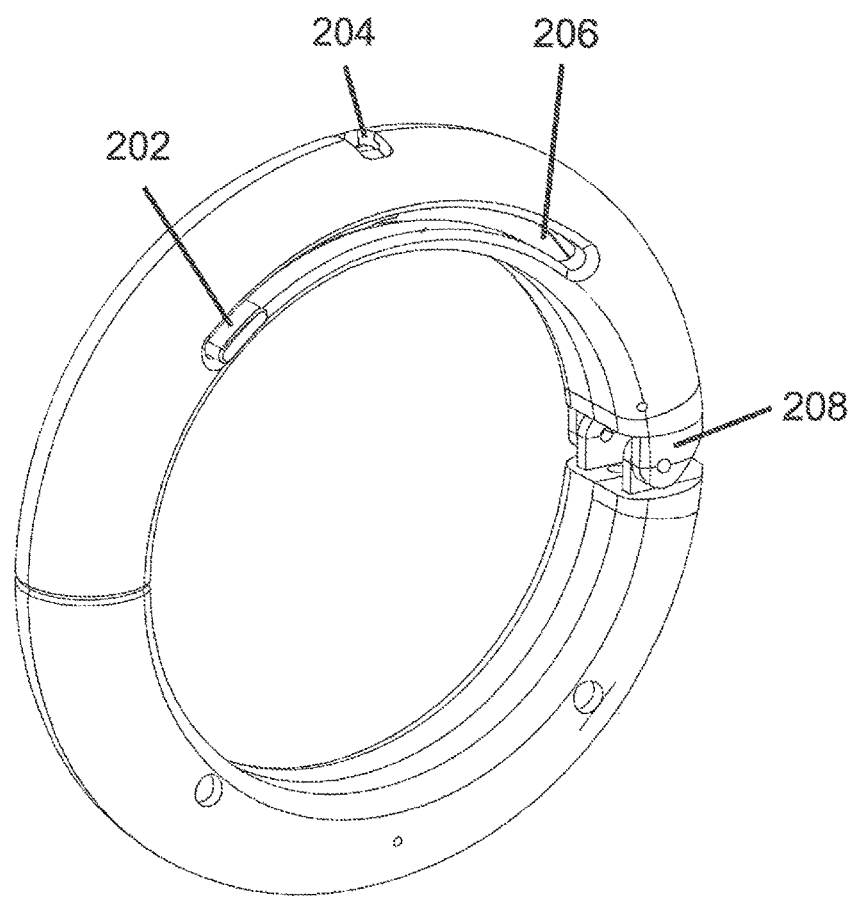
FIG. 2 is a perspective view of the bracelet.
Figure 3:
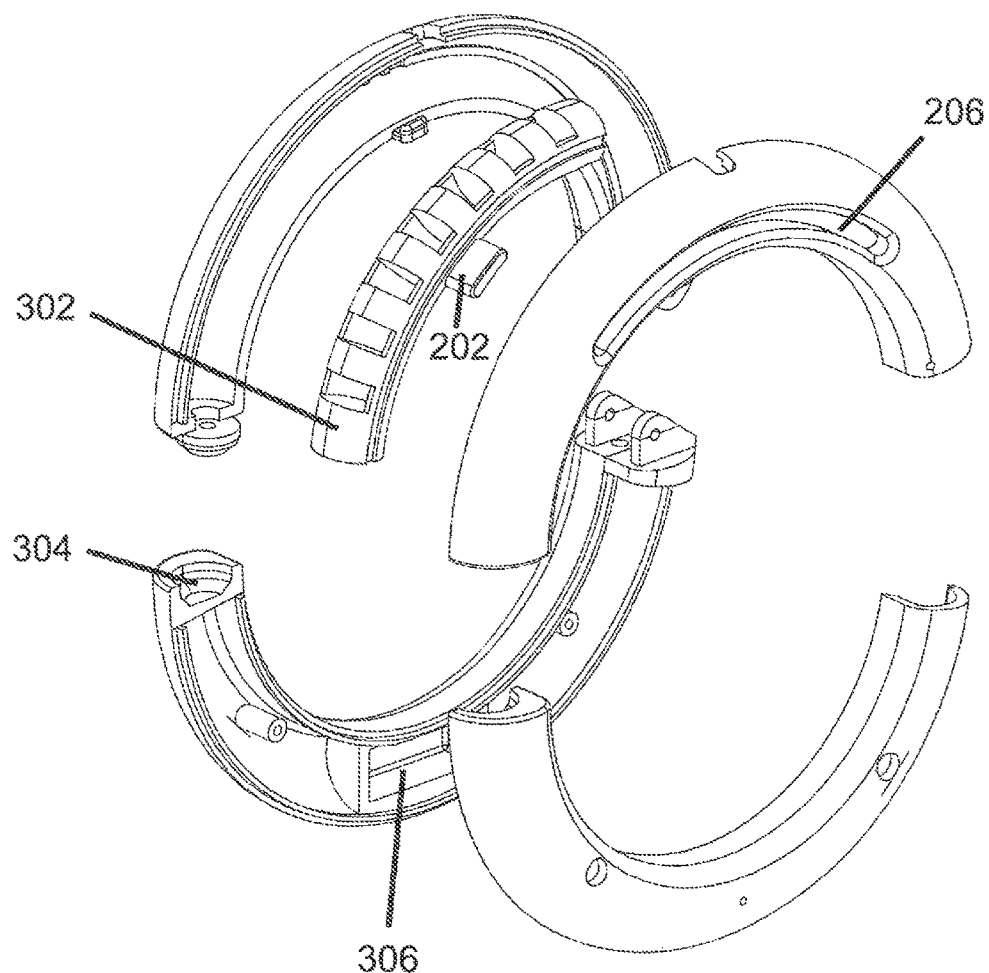
FIG. 3 is an exploded view of the bracelet, showing some interior components that are not shown in the other drawings.
Figure 4:
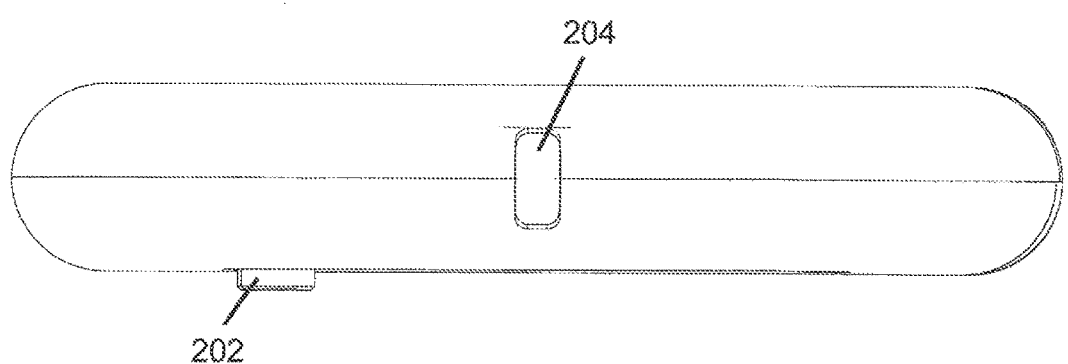
FIG. 4 is a top view of the bracelet.

The following numbers are used in the drawings to illustrate components of the bracelet: button 202, pill door 204, recess 206, bracelet spring hinge 208, medication cartridge 302, bracelet clasp 304, and electronics housing 306 (comprising a printed circuit board, a vibration motor, and other components).

DETAILED DESCRIPTION OF THE INVENTION

A user can dispense a pill from the bracelet by moving the thumb or finger of her free hand to slide the button 202 within the recess 206 to a position that results in pill door 204 to be in an open configuration. In the open configuration of 204, the pill can exit the bracelet. The action of opening and closing door 204 may make a soft clicking sound. The user does not need to remove the bracelet from her hand.

Figure 5:
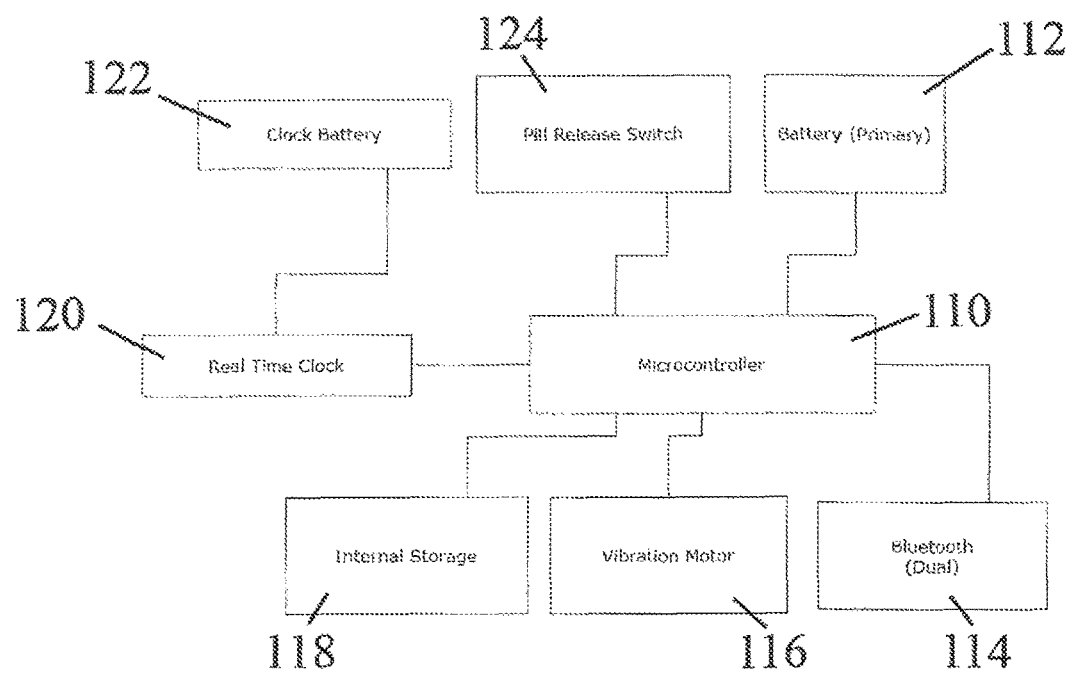
FIG. 5 is a block diagram of selected electronic and mechanical components of the wearable medication dispenser. It comprises a plurality of batteries 112 and/or 122, microcontroller 110, internal storage (e.g., a memory) 118, pill release switch 124. real time clock 120, vibration motor 116, and Bluetooth module 114.

Referring now to the invention in more detail, in FIG. 5 there is shown a microcontroller 110, powered by a battery power source 112, which controls device 10 or device 50 functions. The microcontroller 110 triggers the vibration motor 116 and pill release switch 124 at a specified time each day, which it determines using real time clock 120, in order to remind users to take their medication. The microcontroller 110 records the date and time of dispensing events using real time clock 120, and stores the date and time of the dispensing events on internal storage 118. The date and time information can be transmitted to a wireless phone using bluetooth transmitter 114.

The user can input the alarm reminder time onto her mobile phone (or other Bluetooth-enabled electronic device, for example: a Tablet or a laptop computer). The alarm can be preprogrammed to cause the bracelet to vibrate when the medication should be taken. For example, if the user needs to take the medication at 2:00 PM every day, the user sets the alarm to repeat daily at that time. The microcontroller within the bracelet receives the instruction from the mobile phone via Bluetooth and activates the vibrating alarm at the prearranged time. The user should respond to the alarm by sliding open the pill door on the bracelet and withdrawing the pill into her free hand.

(The present disclosure does not address the question of whether, if the user does not respond, the alarm should go off a second time a few minutes later. Variations on this theme, including a "snooze" button and/or an "alarm off" button, could potentially be adapted from the present disclosure.)

The event of sliding open the door and withdrawing a pill is recorded on an electronic storage medium (also known as "a memory"), and a signal is sent to the user's mobile phone or other Bluetooth-enabled external device, for the purpose of tracking compliance. The user or her designee can monitor compliance using a mobile phone "app" or similar computer program.

The best mode for using the invention involves advance preparation by the user to load a cartridge containing a plurality of pills into a cavity within the interior of the bracelet, and to refill the cartridge after the previous pills have been consumed. In exchange for this preparation and maintenance, the user has access to take the pills at any time and at any place, so long as she is wearing the bracelet. The inventors have produced a prototype comprising a cartridge with seven small compartments intended to hold a one-week supply of pills to be taken once a day. Of course, the number of compartments can vary.

Although the mobile phone must be located near the bracelet in order to facilitate Bluetooth wireless communication (which typically operates at distances of less than ten meters), certain aspects of the bracelet's operation do not depend on the presence of a mobile phone nearby. This is because the electronic chip embedded within the interior of the bracelet comprises a microcontroller connected to the following elements: (1) a clock with a separate clock battery; (2) a primary battery; (3) a pill release switch (activated when the user slides open the door); (4) a vibrating motor (for the alarm); and (5) a Bluetooth module to communicate with an external Bluetooth-enabled device, such as a mobile phone, Tablet or laptop computer. Optionally, the microcontroller can also connect to a sixth element: (6) a memory that can store the data of when the user slid open the door (for the purpose of tracking compliance).

Therefore, if the user remembers to wear her bracelet to work but forgets her mobile phone at home, she should still receive the reminder alarm to take her medication at the prearranged time. The door will still open to allow her to withdraw the medication. It is possible that the electronics inside the bracelet might still record the user sliding open the door and communicate that information to the mobile phone when the Bluetooth connection is reestablished by close proximity (for example, after the forgetful user returns home, where she left her mobile phone in the morning). However, the capability of storing compliance tracking data for future transmission to a mobile phone is not essential to the best mode of using the invention.

Modifications and substitutions by one of ordinary skill in the art are considered to be within the scope of the present invention, which is not to be limited except by the following claims.

The invention claimed is:

1. A medication dispenser bracelet, comprising:
   i) a curved exterior housing, comprising a sliding door, and a button to open and close said door; and
   ii) a removable cartridge in the shape of a curved arc of a size and shape to fit inside said exterior housing, said cartridge comprising a plurality of alternating, equally spaced ridges and valleys aligned serially along a longitudinal axis of the arc, each said valley sized to hold and dispense a medication;
   whereby each manual operation of said button will open said door to dispense a medication from one said valley when that valley is properly aligned under said door.

2. The medication dispenser bracelet of claim 1, further comprising:
   i) a battery;
   ii) an internal time clock; and
   iii) a vibrating motor and alarm-mechanism to alert a wearer of the bracelet to dispense a medication at a preset time.

3. The medication dispenser bracelet of claim 2, further comprising:
   i) a microcontroller;
   ii) a circuit that changes between an open configuration and a closed configuration when the door is opened and closed;
   iii) a sensor to detect when a circuit configuration has changed;
   iv) a memory capable of storing data, said data comprising date and time, for each instance when the circuit configuration has changed; and
   v) a bluetooth device, capable of transmitting data from said memory to an external electronic device, and capable of receiving data from an external electronic device directing the alarm to vibrate at a preset time.

* * * * *